United States Patent [19]

Petusky

[11] Plant 5,018

[45] Mar. 29, 1983

[54] CHRYSANTHEMUM PLANT (CANDLELIGHT)

[76] Inventor: Kerry S. Petusky, 28 W. 748 Barnes Ave., West Chicago, Ill. 60185

[21] Appl. No.: 221,402

[22] Filed: Jan. 8, 1981

[51] Int. Cl.[3] ..... A01H 5/00
[52] U.S. Cl. ..... Plt./74
[58] Field of Search ..... Plt./74

*Primary Examiner*—Robert E. Bagwill

[57] ABSTRACT

A new cultivar of chrysanthemum particularly suitable for six-inch pot plant production, characterized by its single flower form of medium size and unique bronze coloration, its very abundant production of blooms when grown as a spray pot, and its ray florets which are of excellent substance. This variety is also distinguished by its abundant dark green foliage on strong, erect stems and its rapid growth rate. When grown under cool to moderate weather conditions, this variety exhibits a ten-week photoperiodic response.

1 Drawing Figure

BACKGROUND OF THE NEW PLANT

My new variety of pot chrysanthemum was selected by me from a population of seedlings resulting from the hybridization of the variety 'Aglow' (U.S. Plant Pat. No. 3,212) with the variety 'Dramatic' (U.S. Plant Pat. No. 3,189) with the objective of creating new and unusual varieties. This hybridization was performed by me during March 1976, seeds were then harvested and sown and flowered October 1976. From this population of flowering seedlings, this new plant was selected by me and asexually reproduced under my direction and further propagated by means of vegetative cuttings. This work was performed in greenhouses at West Chicago, Ill.

Through successive generations of asexual reproduction, this plant has proved that its distinctive characteristics are firmly fixed and hold true from generation to generation.

DESCRIPTION OF THE DRAWINGS

My new chrysanthemum variety is illustrated by the accompanying full color photographic rendition showing the new variety as it appears as a fully grown potted plant, the colors shown being as nearly true as it is reasonably possible to obtain by conventional photographic procedures.

DESCRIPTION OF THE NEW PLANT

The following is a detailed description of my new variety of chrysanthemum, the color designations being according to the R.H.S. Colour Chart published by The Royal Horticultural Society of London, England.

THE PLANT

Origin: Seedling.
Parentage: Aglow (U.S. Plant Pat. No. 3,212) × Dramatic (U.S. Plant Pat. No. 3,189).
Classification:
*Botanic.*—*Chrysanthemum morifolium.*
*Commercial.*—Greenhouse pot plant.
Form: Vase-shaped, perennial herbaceous bush.
Height: Varies with cultural practices.
Growth: Upright and vigorous, sturdy, with very good strength.
Branching: Normal under natural conditions.

Foliage:
*Quantity.*—Abundant, 7 to 10 leaves on 10 cm. of stem.
*Leaf size.*—Length — Approximately 8.5 to 12.0 cm. (typical mature leaf). Width — Approximately 5.0 to 7.0 cm. (typical mature leaf).
*Shape.*—Lobed, rather deeply cleft and slightly serrated.
*Texture.*—Canescent.
*Color.*—Upper side — 147A. Under side — 147B.
*Venation.*—Pinnate.
*Petioles.*—Length — Approximately 1.2 to 2.0 cm.

THE BUD

Form: Globular.
Size: Varies in both diameter and depth.
Opening rate: Slow, typical chrysanthemum.
Color:
*When phyllaries first divide.*—11A.
*When florets begin to unfurl.*—17A.
Phyllaries: Many involucral, upstanding bracts on the outside of the receptacle.
*Shape.*—Spear-shaped.
*Color.*—Inside — 138A. Outside — 137B.
*Surface texture.*—Pubescent.
Peduncle: Sturdy and erect.
*Length.*—Varies considerably.
*Surface texture.*—Canescent.
*Color.*—138B.

THE FLOWER

Response: 10 week.
Recommended flowering: Approximately September 15 to June 15 for Northern U.S.A. with photoperiodic control. Not recommended for production in very warm environments.
Blooms:
*Type.*—Single and composite.
*Borne.*—A head of many florets borne on a receptacle.
*Shape.*—Cup-shaped when bloom first opens, becoming almost flat upon maturation.
*Size.*—Medium-size bloom. Diameter — Approximately 4.5 to 7.5 cm. Depth — Approximately 1.2 to 2.3 cm.
Florets:
*Quantity.*—Numerous.

*Form.*—Linear with obtuse apex.

*Firmness.*—Very firm.

*Appearance.*—Very slight shine.

*Color.*—Ray florets — Upper side: 14A, 14B, 17B. Reverse side: 13C, 15D. Disc florets — 6A. Discoloration — Slight fade as full bloom ages.

Persistence: Flowers hang on and dry.

Lasting quality:

*On plant.*—4 weeks. Not recommended for cut-flower use.

REPRODUCTIVE ORGANS

Stamens:

*Quantity.*—5 to each disc floret.

*Arrangement.*—Syngenesious.

*Filaments.*—Length — 3 to 5 mm. Color — yellow.

*Pollen.*—Color — yellow.

Pistils: Number — One to each ray and disc floret.

*Styles.*—Length — 5 to 6 mm.

*Stigmas.*—Color — yellowish-green.

Ovaries: Inferior bicarpellate.

This new variety of chrysanthemum is particularly characterized by its single flower form with very firm ray florets of a unique bronze coloration which do not reflex upon maturation. Because of its vigorous growth rate, it is particularly suitable for six-inch, tall treatment, pot production.

Flowering is delayed when grown under very warm temperatures, thus it is recommended for spring, fall and winter flowering at which times it responds as a ten-week variety with photoperiodic control.

I claim:

1. A new and distinctive cultivar of chrysanthemum, substantially as herein shown and described, particularly characterized by its single flower form, medium flower size, flowers which exhibit bronze coloration and excellent substance, abundant foliage and its applicability for six-inch pot production.

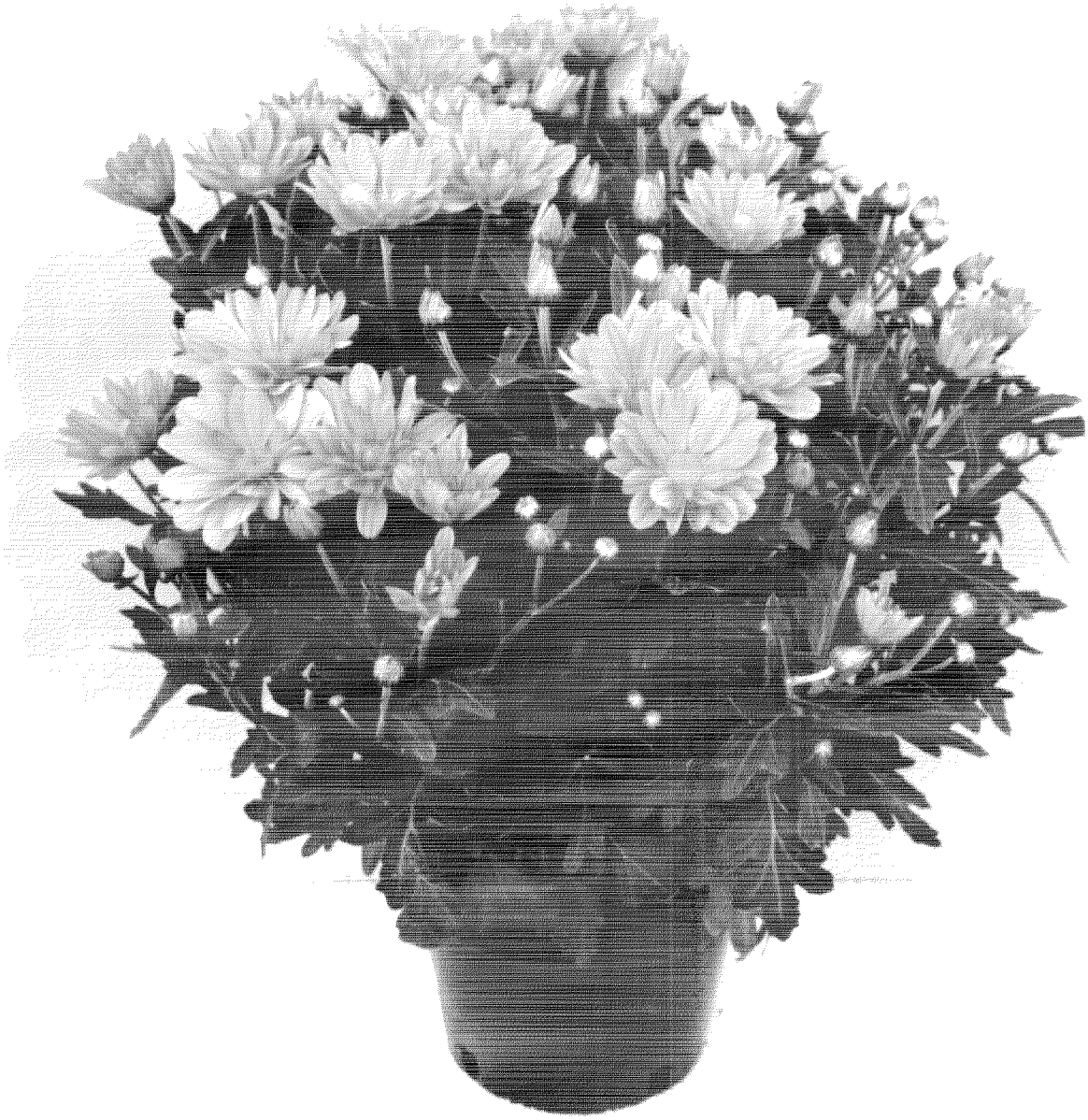

* * * * *